United States Patent [19]

Egan et al.

[11] Plant 4,131

[45] Oct. 18, 1977

[54] CHRYSANTHEMUM PLANT

[75] Inventors: William H. Egan, Brooks, Oreg.; Jack M. Meek, Barberton; William E. Duffett, Akron, both of Ohio

[73] Assignee: William H. Egan, Brooks, Oreg.

[21] Appl. No.: 720,501

[22] Filed: Sept. 3, 1976

[51] Int. Cl.[2] ..... A01H 5/00

[52] U.S. Cl. ..... Plt./75

[58] Field of Search ..... Plt./75, 78

*Primary Examiner*—Robert E. Bagwill

*Attorney, Agent, or Firm*—Donald D. Jeffery

[57] ABSTRACT

This novel mutation of Cloud-9 differs therefrom by its yellow blossoms.

2 Drawing Figures

1

The present invention comprises a new and distinct cultivar of *Chrysanthemum morifolium,* Ramat., hereinafter referred to by the cultivar named Yellow Cloud-9 (No. 2166BE15).

Yellow Cloud-9 is a spontaneous sport of Cloud-9 (No. 21660E15: U.S. Plant Pat. No. 3,500). Yellow Cloud-9 was discovered and selected by William H. Egan in 1973 as three plants within a flowering block of Cloud-9 in an outdoor field in Brooks, Oreg.

The first act of asexual reproduction of Yellow Cloud-9 was accomplished when vegetative cuttings were taken from the initial selection in July, 1974 in a controlled environment in Barberton, Ohio by a technician working under formulations established and supervised by Jack M. Meek and William E. Duffett. Horticultural examination of selected units initiated Oct. 7, 1974 has demonstrated that the combination of characteristics as herein disclosed for Yellow Cloud-9 are firmly fixed and are retained through successive generations of asexual reproduction.

Yellow Cloud-9 has not been observed under all possible environmental conditions. The phenotype may vary significantly with variations in environment such as temperature, light intensity, and daylength. The following observations, measurements, and comparisons describe plants grown in a field in Barberton, Ohio under conditions which are generally described in *Local Climatological Data, Annual Summary With Comparative Data, Akron, Ohio,* U.S. Department of Commerce, National Oceanic and Atmospheric Administration, Environmental Data Service, Washington, D.C. 1974, 1975, 1976, and *Tables of Sunrise, Sunset, and Twilight,* supplement to the American Emphemeris, 1946., U.S. Naval Observatory, Washington, D.C., pg. 103.

The following traits have been repeatedly observed and are determined to be basic characteristics of Yellow Cloud-9 which in combination distinguish this chrysanthemum as a new and distinct cultivar:

2

1. Incurved inflorescence form, reflexing rapidly with age.
2. Decorative inflorescence type.
3. Dark yellow inflorescence color with minimal color oxidation.
4. Diameter across face of inflorescence up to 130 mm.
5. Permanence of inflorescence ranging up to 10 days.
6. Short plant height (requiring 2–3 long day weeks prior to short days and 1–2 applications of 2500 ppm B9-SP to attain a flowered plant height of 30 to 45 cm.)
7. Spreading branching pattern.
8. Average natural season flowering date of Sept. 25.
9. Average flowering response period of 7 weeks in photo-periodic controlled flowering programs.

The accompanying photographic drawings show typically inflorescence and foliage characteristics of Yellow Cloud-9. Sheet 1 is a color photograph of Yellow Cloud-9. Sheet 2 is a black and white photograph showing the foliage of Yellow Cloud-9 at three stages of growth.

Of the many commercial cultivars known to the present inventors, the most similar existing cultivar in comparison to Yellow Cloud-9 is the parental cultivar, Cloud-9. Reference is made to attached Chart A which compares certain characteristics of Yellow Cloud-9 and Cloud-9. It will be noted that Yellow Cloud-9 has different inflorescence color than Cloud-9. The inflorescence form, inflorescence type, average natural season flower date, plant height, diameter across face of inflorescence, and branching pattern of Yellow Cloud-9 are similar to those same characteristics of Cloud-9.

In the following description, color references are made to The Munsell Limit Color Cascade, 1972 edition. The color values were determined between 12:00 and 12:30 P.M. on May 20, 1976 under 200 foot-candle light intensity at Barberton, Ohio.

CHART A

COMPARISON OF YELLOW CLOUD-9 AND CLOUD-9

| CULTIVAR | INFLORESCENCE COLOR | INFLORESCENCE FORM AND TYPE | AVERAGE NATURAL SEASON FLOWER DATE | PLANT HEIGHT | DIAMETER ACROSS FACE OF INFLORESCENCE | BRANCHING PATTERN |
|---|---|---|---|---|---|---|
| Yellow Cloud-9 | Dark Yellow | Incurved Decorative | September 25 | Short | 95 to 130 mm. | Spreading |
| Cloud-9 | Ivory White | Incurved Decorative | September 25 | Short | 115 to 130 mm. | Spreading |

COMPARISONS MADE OF PLANTS GROWN UNDER NATURAL SEASON OUTDOOR FIELD CONDITIONS IN BARBERTON, OHIO.

Botanical classification: *Chrysanthemum morifolium,* Ramat., cv Yellow Cloud-9.

INFLORESCENCE (See Sheet 1 of drawings)

Capitulum:

*Form.*—Incurved, reflexing rapidly with age.

*Type.*—Decorative.

*Permanence.*—10 days.

*Diameter (face).*—95 to 130 mm.

Corolla of ray florets:

*Color (abaxial).*—27-5 to 25-4.

*Color (adaxial).*—25-5 to 25-3.

Reproductive organs:

*Androecium.*—Present disc florets only; scant pollen.

*Gynoecium.*—Present both ray and disc florets.

PLANT (See Sheets 1 and 2 of drawings)

General appearance: Spreading branching pattern; short height.

Foliage:

*Color (abaxial).*—Approximately 21-13 to 21-15 overlaid with grey.

*Color (adaxial).*—Approximately 21-13 overlaid with grey.

We claim:

1. A new and distinct cultivar of chrysanthemum known by the cultivar name Yellow Cloud-9 and characterized particularly as to uniqueness by the combined characteristics of incurved inflorescence form, reflexing rapidly with age; decorative inflorescence type; dark yellow inflorescence color with minimal color oxidation; diameter across face of inflorescence up to 130 mm.; permanence of inflorescence ranging up to 10 days; short plant height; spreading branching pattern; average natural season flower date of Sept. 15; and average flowering response period of 7 weeks in photoperiodic controlled flowering programs.

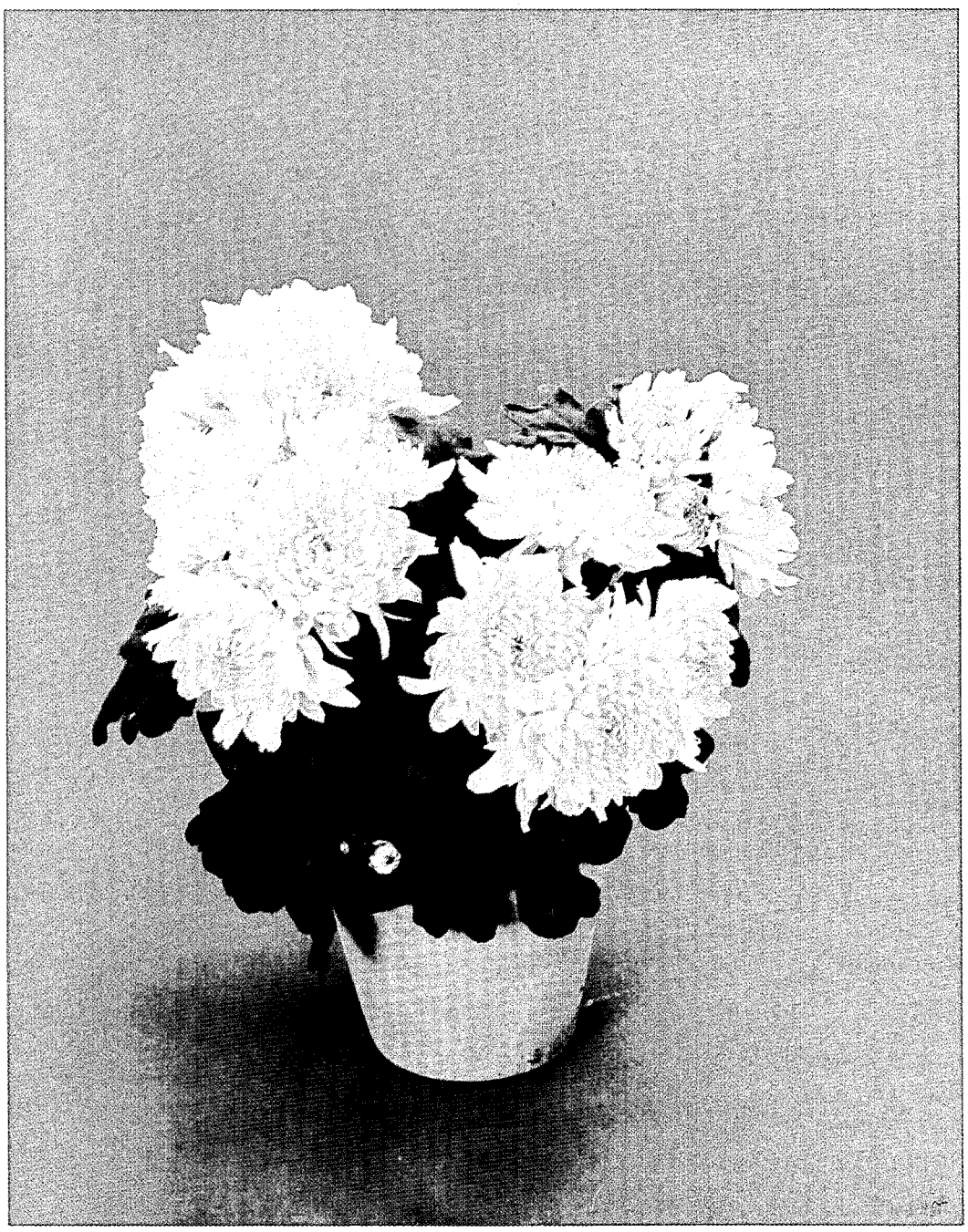

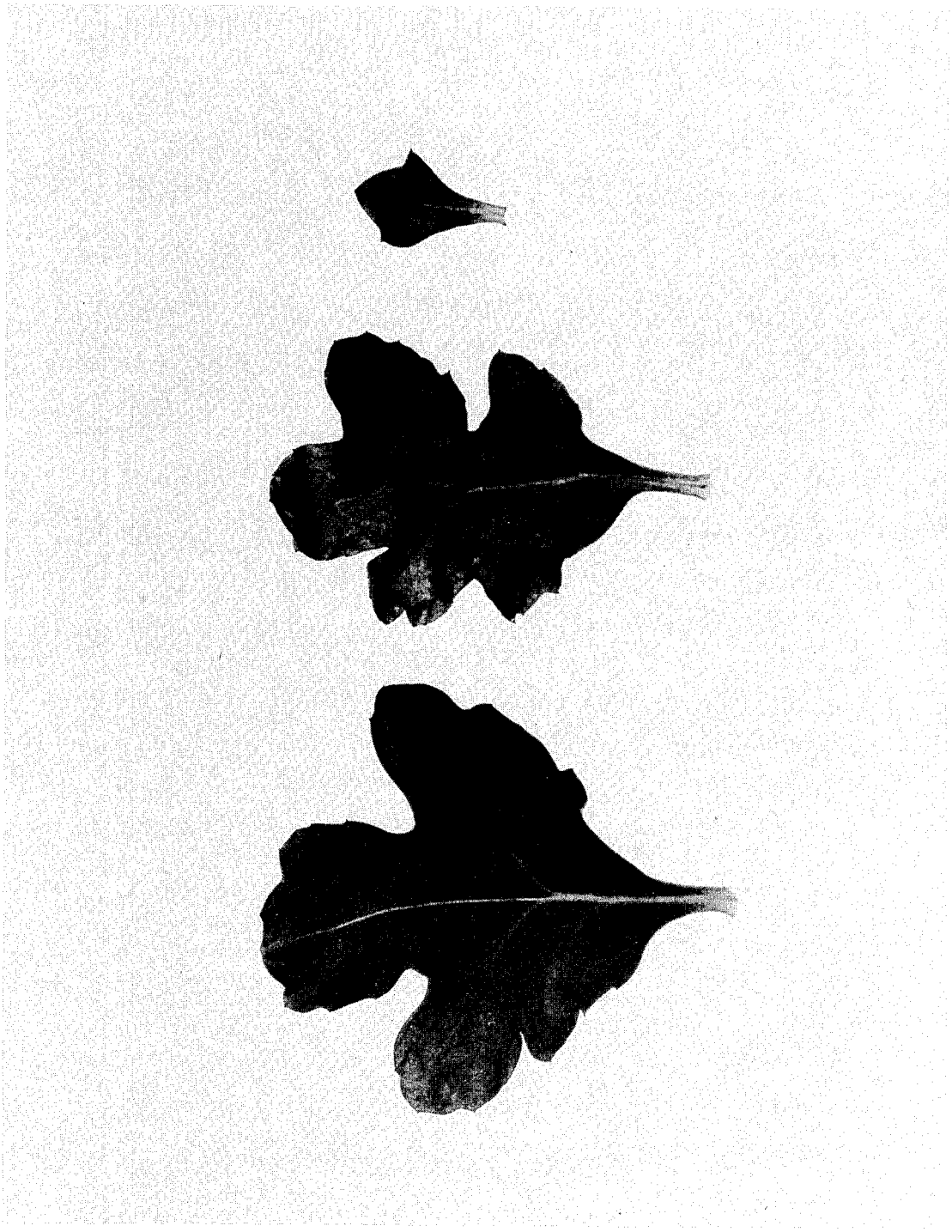

* * * * *